United States Patent
Schelges et al.

(10) Patent No.: US 10,639,246 B2
(45) Date of Patent: May 5, 2020

(54) CLEANSING COMPOSITION WITH HIGH FATTY ACID CONTENT

(71) Applicant: Henkel AG & Co. KGaA, Duesseldorf (DE)

(72) Inventors: Heike Schelges, Willich (DE); Evelyn Domfeld, Duesseldorf (DE)

(73) Assignee: Henkel AG & Co. KGaA (DE)

( * ) Notice: Subject to any disclaimer, the term of this patent is extended or adjusted under 35 U.S.C. 154(b) by 0 days.

(21) Appl. No.: 14/974,100

(22) Filed: Dec. 18, 2015

(65) Prior Publication Data

US 2016/0101027 A1    Apr. 14, 2016

Related U.S. Application Data

(63) Continuation of application No. PCT/DE2014/200276, filed on Jun. 23, 2014.

(30) Foreign Application Priority Data

Jul. 2, 2013 (DE) .................. 10 2013 212 873

(51) Int. Cl.

| | |
|---|---|
| *A61K 8/04* | (2006.01) |
| *A61K 8/44* | (2006.01) |
| *A61Q 19/10* | (2006.01) |
| *A61Q 19/00* | (2006.01) |
| *A61K 8/86* | (2006.01) |
| *A61K 8/46* | (2006.01) |
| *A61Q 5/12* | (2006.01) |
| *A61Q 5/02* | (2006.01) |
| *A61K 8/36* | (2006.01) |

(52) U.S. Cl.
CPC .............. *A61K 8/046* (2013.01); *A61K 8/361* (2013.01); *A61K 8/442* (2013.01); *A61K 8/463* (2013.01); *A61K 8/86* (2013.01); *A61Q 5/02* (2013.01); *A61Q 5/12* (2013.01); *A61Q 19/007* (2013.01); *A61Q 19/10* (2013.01); *A61K 2800/49* (2013.01); *A61K 2800/5422* (2013.01); *A61K 2800/5424* (2013.01); *A61K 2800/5428* (2013.01); *A61K 2800/596* (2013.01)

(58) Field of Classification Search
CPC ........ A61K 2800/49; A61K 2800/5422; A61K 2800/5424; A61K 2800/5428; A61K 2800/596; A61K 8/361; A61K 8/463; A61K 8/86; A61Q 19/007; A61Q 19/10; A61Q 5/02; A61Q 5/12
See application file for complete search history.

(56) References Cited

U.S. PATENT DOCUMENTS

| | | | |
|---|---|---|---|
| 2003/0175232 A1* | 9/2003 | Elliott | ................ A61K 8/0208 424/70.14 |
| 2004/0170670 A1* | 9/2004 | Smith | ..................... A47K 7/02 424/443 |

FOREIGN PATENT DOCUMENTS

| | | | | |
|---|---|---|---|---|
| DE | 10156674 | A1 | 5/2003 | |
| EP | 2314270 | A2 | 4/2011 | |
| WO | 92/13829 | A1 | 8/1992 | |
| WO | 01/13877 | A1 | 3/2001 | |
| WO | WO 01/13877 | * | 3/2001 | ............. A61K 7/48 |
| WO | 02/05758 | A2 | 1/2002 | |
| WO | 2008/038147 | A2 | 4/2008 | |
| WO | 2013/012420 | A1 | 1/2013 | |

OTHER PUBLICATIONS

Fruijtier-Pollöth (Toxicology 214(2005) 1-38). (Year: 2005).*
Romaskevie et al. (Chemija. 2006. vol. 17, No. 4. pp. 74-89) (Year: 2006).*
PCT International Search Report (PCT/DE2014/200276) dated Oct. 11, 2014.

* cited by examiner

*Primary Examiner* — Anna R Falkowitz
(74) *Attorney, Agent, or Firm* — James J. Cummings

(57) ABSTRACT

A cosmetic cleansing composition includes a) 0.1 to 30 wt. %, based on the total weight of the cleansing composition, of a surfactant selected from the group of anionic, non-ionic, and/or zwitterionic surfactants and mixtures thereof, b) at least one partially and/or non-neutralized, unbranched, saturated and/or unsaturated carboxylic acid with a chain length of 14 to 30 carbon atoms, and c) at least one non-ionic polymer of the formula (I) as set forth herein, where R represents a hydrogen atom or a methyl group and n represents a whole number value from 1,360 to 99,000. The cleansing composition has a mousse-like texture and excellent cleansing and care properties.

10 Claims, No Drawings

CLEANSING COMPOSITION WITH HIGH FATTY ACID CONTENT

FIELD OF THE INVENTION

The present invention generally relates to cosmetic cleansing compositions that have a high fatty acid content, and also those that have excellent foaming properties and a mousse-like texture.

The present invention also relates to the use of such cleansing compositions for cleansing and caring for skin and hair.

BACKGROUND OF THE INVENTION

Cleansing compositions such as cosmetic cleansing compositions for the skin and the hair include liquid soaps, shampoos, bath soaks, foam bath products, shower and washing gels. In addition to having good cleansing capability, these cleansing compositions must also be able to prevent excessive degreasing or drying of the skin that would otherwise result from frequent application. Furthermore, the cleansing compositions should be appealing visually and, from a sensory viewpoint, should be comfortably handled.

Some cleansing compositions that have a light texture are used in the form of a mousse and are appealing visually. These mousse products are characterized by simple application and have a high cleansing capability due in part to their easy distribution about the hair. In addition, the ingredients of the mousse soak in quickly, thus increasing the care properties. Furthermore, the mousse does not produce a slimy or sticky feel on the application surface after it has been rinsed off.

In order to avoid excessive degreasing or skin dryness in the event of frequent application, while satisfying the demands of the consumer in respect of the simultaneous cleansing and care, regreasing agents such as linear or branched carboxylic acids are incorporated into the mousse. Non- and/or partially neutralized carboxylic acids, however, reduce the mousse foaming capability and therefore the cleansing capability of the mousse.

Thus, cleansing compositions have been developed in the prior art that have a mousse-like texture with use of non- and/or partially neutralized fatty acids as regreasing agents. International patent application WO 2013/012420 A1 describes aqueous cleansing compositions having a mousse-like texture which, besides fatty acid soaps, also include non-neutralized fatty acids. The mousse-like texture is achieved by use of bivalent metal cations, which enclose a gas in the cleansing compositions. However, the use of fatty acid soaps in combination with bivalent metal cations is associated with the formation of lime soaps, which are difficult to dissolve, cause deposits, which are not very visually appealing, on the skin and hair and other surfaces, and reduce the cleansing performance of the mousse.

There is thus a need for cosmetic skin and hair cleansing compositions which have a mousse-like texture and at the same time cleanse to an excellent level. In addition, such compositions should have excellent foaming properties, which are reflected in the foam volume, a stable foam, and improved sensory and visual properties of the foam. In addition, the cosmetic skin and hair cleansing compositions should have a high proportion of regreasing non- and/or partially neutralized carboxylic acids in order to increase the care properties.

It is therefore desirable to provide cosmetic cleansing compositions which have excellent foaming properties, which cleanse the skin and hair gently and thoroughly, and provide excellent care on account of the high proportion of regreasing and non- and/or partially neutralized carboxylic acids.

Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

It has now been found that the use of high-molecular non-ionic polymers leads to cleansing compositions which, in spite of the high proportion of regreasing and non- and/or partially neutralized carboxylic acids, have excellent foaming, cleansing and care properties.

An exemplary cosmetic cleansing composition contains 0.1 to 30 wt. %, based on the total weight of the cleansing composition, of a surfactant selected from the group of anionic, non-ionic and/or zwitterionic surfactants and mixtures thereof; at least one partially and/or non-neutralized, unbranched, saturated and/or unsaturated carboxylic acid with a chain length of 14 to 30 carbon atoms; and at least one non-ionic polymer of formula (I)

wherein R represents a hydrogen atom or a methyl group and n represents a whole number value from 1,360 to 99,000.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

The subject of the present invention is a cosmetic cleansing composition, that includes:
a) 0.1 to 30 wt. %, based on the total weight of the cleansing composition, of a surfactant selected from the group of anionic, non-ionic and/or zwitterionic surfactants and mixtures thereof,
b) at least one partially and/or non-neutralized, unbranched, saturated and/or unsaturated carboxylic acid with a chain length of 14 to 30 carbon atoms, and
c) at least one non-ionic polymer of formula (I)

wherein R represents a hydrogen atom or a methyl group and n represents a whole number value from 1,360 to 99,000.

The cleansing compositions of the present invention are in the form of a mousse having a visually appealing texture and have a sufficiently high stability to be packaged, stored and marketed as a mousse. The mousse is stable and can be spread easily on the skin/the hair. Due to the small pore size of the foam, the mousse feels creamy, which makes the care effect noticeable during the cleansing process. Furthermore, the mousse can be rinsed off again quickly and thoroughly following the cleansing, without leaving behind a slimy or sticky feel on the surface to which it was applied. In addition, the cleansing compositions according to the invention have a high caring nature on account of the high proportion of regreasing non- and/or partially neutralized carboxylic acids, such that excessive degreasing or drying of the skin is avoided in the event of frequent application.

The term mousse, as used in accordance with the invention, is to be understood to mean cleansing compositions which, following the production process or in the event of application by the consumer, have a foamy, cream-like consistency. Cleansing compositions of this type have an arbitrary distribution of spherical or polyhedral cells filled with gas, which are delimited by liquid, semi-liquid or highly viscous cell walls formed from a mixture of surfactants, water and further auxiliaries.

Furthermore, the term fatty acid as used within the scope of the present invention is to be understood to mean aliphatic carboxylic acids comprising unbranched carbon groups with 4 to 40 carbon atoms. The fatty acids used within the scope of the present invention may be both naturally occurring and synthetically produced fatty acids. The fatty acids may also be unsaturated once or more.

In addition, the term fatty alcohol is to be understood within the scope of the present invention to mean aliphatic, monovalent, primary alcohols comprising unbranched hydrocarbon groups with 4 to 40 carbon atoms. The fatty alcohols used within the scope of the invention may also be unsaturated once or more.

In order to attain an excellent cleansing performance and particularly good foaming properties, a mixture of at least one anionic and at least one non-ionic and/or zwitterionic surfactant is used in an embodiment that is preferred in accordance with the invention, wherein the weight ratio of the anionic surfactant(s) to the non-ionic and/or zwitterionic surfactant(s) is from 3:1 to 1:2, preferably 2:1 to 1:1.5, and in particular 1.5:1 to 1:1.

In this context, in accordance with the invention, the anionic surfactant may additionally be contained in the cleansing composition according to the invention in a quantity of 0.1 to 50 wt. %, preferably 0.2 to 40 wt. %, more preferably 0.3 to 30 wt. %, even more preferably 0.4 to 20 wt. %, and in particular 0.5 to 15 wt. %, based on the total weight of the cleansing composition.

In accordance with a further embodiment of the present invention, the non-ionic and/or zwitterionic surfactant may be contained in the cleansing composition according to the invention in a quantity of 0.1 to 20 wt. %, preferably 0.2 to 18 wt. %, more preferably 0.3 to 15 wt. %, and in particular 0.5 to 10 wt. %, based on the total weight of the cleansing composition.

All anionic surfactants or surface-active substances suitable for use on the human body can be used as anionic surfactants in the cleansing compositions according to the invention. These are characterized by a hydrophilic anionic group, such as a carboxylate, sulfate, sulfonate or phosphate group and a lipophilic alkyl group with approximately 8 to 30 carbon atoms. In addition, the surfactants may comprise glycol or polyglycol ether groups, esther, ether and amide groups, and hydroxyl groups.

Anionic surfactants that are suitable in accordance with the invention are, in each case in the form of the sodium, potassium and ammonium salts and also the mono-, di- and triaklanolammonium salts with 2 to 4 carbon atoms in the alkanol group, linear and branched fatty acids with 8 to 30 carbon atoms (soaps),
ether carboxylic acids of the formula (TI)

$$R^1O-(CH_2CH_2O)_x-CH_2-COOH \qquad (TI)$$

in which $R^1$ is a linear alkyl group with 8 to 30 carbon atoms and x=0 or is 1 to 16,
acyl sarcosine with 8 to 24 carbon atoms in the acyl group,
acyl taurine with 8 to 24 carbon atoms in the acyl group,
acyl isethionate with 8 to 24 carbon atoms in the acyl group,
sulfosuccinic acid mono- and dialkyl esters with 8 to 24 carbon atoms in the alkyl group and sulfosuccinic acid monoalkylpolyoxyethylester with 8 to carbon atoms in the alkyl group and 1 to 6, preferably 1 to 4 oxyethyl groups,
linear alkane sulfonates with 8 to 24 carbon atoms,
linear alpha-olefin sulfonates with 8 to 24 carbon atoms,
alpha-sulfonic fatty acid methyl esters of fatty acids with 8 to 30 carbon atoms,
alkyl sulfates and alkyl polyglycol ether sulfates of the formula (TII)

$$R^2-O(CH_2-CH_2O)_x-SO_3H \qquad (TII)$$

in which $R^2$ is a preferably linear alkyl group with 8 to 30 carbon atoms and x=0 or is 1 to 14,
mixtures of surface-active hydroxysulfonates,
sulfated hydroxyalkyl polyethylene and/or hydroxyalkylene propylene glycol ethers,
sulfonates of unsaturated fatty acids with 8 to 24 carbon atoms and 1 to 6 double bonds,
esters of tartaric acid and citric acid with alcohols, which represent addition products of approximately 2 to 15 molecules of ethylene oxide and/or propylene oxide onto fatty alcohols with 8 to 22 carbon atoms,
alkyl and/or alkenyl ether phosphates of formula (TIII),

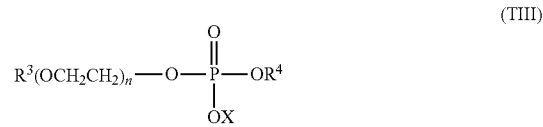

$$R^3(OCH_2CH_2)_n-O-\overset{\overset{O}{\|}}{\underset{OX}{P}}-OR^4 \qquad (TIII)$$

in which $R^3$ is preferably an aliphatic hydrocarbon group with 8 to 30 carbon atoms, X is hydrogen, an alkaline or alkaline earth metal or $NR^5R^6R^7R^8$, with $R^5$ to $R^8$ independently of one another representing a $C_1$ to $C_4$ hydrocarbon group, $R^4$ is hydrogen, a group $R^3(CH_2CH_2O)_n$ or X and n=1 to 10,
sulfated fatty acid alkylene glycol esters of formula (TIV)

$$R^9CO\text{-}(Alk\text{-}O)_n-SO_3M \qquad (TIV)$$

in which $R^9$ represents a linear or branched, aliphatic, saturated and/or unsaturated acyl group with 6 to 22 carbon atoms, Alk represents $CH_2CH_2$, $CHCH_3CH_2$ and/or $CH_2CHCH_3$, n represents numbers from 0.5 to 5, and M represents a cation, as described in DE-OS 197 36 906 5,
monoglyceride sulfates and monoglyceride (ether) sulfates of the formula (TV),

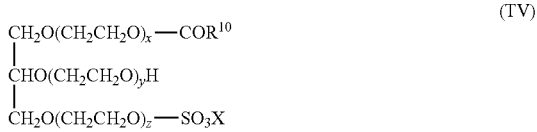 (TV)

in which $R^{10}$ represents a linear or branched acyl group with 6 to 22 carbon atoms, x, y and z in total represent 0 or numbers from 1 to 30, preferably 2 to 10, and X represents an alkaline or earth alkaline metal.

Typical examples for monoglyceride (ether) sulfates in the form of their sodium salts suitable within the context of the invention include the reaction products of lauric monoglyceride, cocoa fatty acid monoglyceride, palmitic acid monoglyceride, stearic acid monoglyceride, oleic acid monoglyceride and tallow fatty acid monoglyceride as well as their ethylene oxide adducts with sulfur trioxide or chlorosulfonic acid.

Preferably, monoglyceride sulfates of formula (TV) are added, in which R10 represents a linear acyl group with 8 to 18 carbon atoms.

In accordance with a preferred embodiment of the present invention the at least one anionic surfactant is selected from the group of alkyl polyglycol ether sulfates, alkyl sulfates and/or sulfosuccinic acid monoalkyl polyoxyethyl esters with 8 to 18 carbon atoms in the alkyl group and 1 to 10, preferably 1 to 4 oxyethyl groups in the polyoxyethyl group. The aforementioned surfactants have properties that are particularly mild on the skin, such that irritation of the skin is avoided, even with frequent application.

In accordance with the invention, non-ionic and/or zwitterionic surfactants are also used. The non-ionic surfactants have, as hydrophilic group, for example a polyol group, a polyalkylene glycol ether group, or a combination of polyol and polyglycol ether group.

Non-Ionic surfactants that are suitable in accordance with the invention include for example addition products of 2 to 50 mol ethylene oxide and/or 0 to 5 mol propylene oxide onto linear and branched fatty alcohols with 8 to 30 carbon atoms, onto fatty acids with 8 to 30 carbon atoms, and onto alkyl phenols with 8 to 15 carbon atoms in the alkyl group, addition products, closed at the end group by a methyl or $C_2$ to $C_6$ alkyl group, of 2 to 50 mol ethylene oxide and/or 0 to 5 mol propylene oxide onto linear and branched fatty alcohols with 8 to 30 carbon atoms, onto fatty acids with 8 to 30 carbon atoms, and onto alkyl phenols with 8 to 15 carbon atoms in the alkyl group, such as the types obtainable under the trade names Dehydol® LS, Dehydol® LT (Cognis), $C_{12}$-$C_{30}$ carboxylic acid monoesters and diesters of addition products of 1 to 30 mol ethylene oxide onto glycerol, addition products of 5 to 60 mol ethylene oxide onto castor oil and hydrogenated castor oil, polyol fatty acid esters, such as the commercial product Hydagen® HSP (Cognis) or Sovermol types (Cognis), alkoxylated triglycerides, alkoxylated fatty acid alkyl esters of the formula (TVI)

$R^{11}CO\text{—}(OCH_2CHR^{12})_wOR^{13}$ (TVI)

in which $R^{11}$ represents a linear or branched, saturated and/or unsaturated acyl group with 6 to 22 carbon atoms, $R^{12}$ represents hydrogen or methyl, $R^{13}$ represents linear or branched alkyl groups with 1 to 4 carbon atoms, and w represents numbers from 1 to 20, amine oxides, hydroxy mixed ethers, as described for example in DE-OS 19738866, sorbitan fatty acid esters and addition products of ethylene oxide on sorbitan fatty acid esters, such as polysorbates, sugar fatty acid esters and addition products of ethylene oxide on sugar fatty acid esters, fatty acid N-alkyl glucamides.

A further group of non-ionic surfactants suitable in accordance with the invention is constituted by alkyl polyglucosides.

These correspond to the formula (TVII)

$R^{14}O\text{-}[G]_p$ (TVII)

in which $R^{14}$ represents an alkyl and/or alkenyl group with 4 to 22 carbon atoms, G represents a sugar group with 5 or 6 carbon atoms, and p represents numbers from 1 to 10. The index number p in the general formula (TVII) specifies the degree of oligomerization (DP), i.e. the distribution of monoglucosides and oligoglucosides, and represents a number between 1 and 10. Whereas p in a given compound must always be a whole number, and here in particular may assume the values p=1 to 6, the value p is an analytically determined mathematical variable for a certain alkyl oligoglucoside and usually represents a fractional number. In accordance with the invention alkyl and/or alkenyl oligoglucosides having a mean degree of oligomerization p from 1.1 to 3.0 are preferably used. In terms of application, alkyl and/or alkenyl oligoglucosides of which the degree of oligomerization is less than 1.7 and in particular lies between 1.2 and 1.7 are preferred. The alkyl or alkenyl group $R^{14}$ may derive from primary alcohols with 4 to 20, preferably 8 to 16 carbon atoms. In accordance with the invention, alkyl oligoglucosides based on hydrogenated $C_{12/14}$ coconut alcohol having a DP from 1 to 3 are especially preferred, as are available commercially for example under the INCI name "Coco-glucoside".

Surface-active compounds comprising at least one quaternary ammonium group and at least one $\text{—COO}^{(-)}$ or $\text{—SO}_3^{(-)}$ group are referred to as zwitterionic surfactants. Particularly preferred zwitterionic surfactants are what are known as betaines, such as N-alkyl-N,N-dimethylammonium glycinates, for example the coconut alkyl dimethylammonium glycinate, N-acylaminopropyl-N,N-dimethylammonium glycinate, for example coconut acylaminopropyl dimethylammonium glycinate and 2-alkyl-3-carboxymethyl-3-hydroxyethyl imidazolines, each with 8 to 18 carbon atoms in the alkyl or acyl group, and coconut acylamino ethylhydroxyethyl carboxymethyl glycinate. Particularly preferred zwitterionic surfactants in accordance with the invention are the carboxylic acid amide derivative and alkyl betaines with 10 to 20 carbon atoms in the alkyl group known under the INCI name cocamidopropyl betaine.

In accordance with a preferred embodiment of the present invention the at least one non-ionic surfactant can be selected from the group of polyethoxylated carboxylic acid esters or fatty acid esters with a chain length from 8 to 30 carbon atoms and a degree of ethoxylation from 5 to 50, ethoxylated glyceryl carboxylic acid esters with a degree of ethoxylation from 2 to 20, and alkyl oligoglucosides with 8 to 16 carbon atoms in the alkyl group. The at least one zwitterionic surfactant can also be selected from the group of $C_{8-18}$ alkylamido ($C_{1-4}$) alkyl betaines.

In a particularly preferred embodiment of the present invention the cosmetic cleansing compositions contain a mixture of alkyl polyglycol ether sulfates and alkyl amido alkyl betaines or alkyl oligoglucosides (as already defined), which are characterized by outstanding mildness on the skin and excellent foam development and foam quality.

As second mandatory component b), the cleansing compositions according to the invention contain at least one partially and/or non-neutralized, unbranched, saturated and/or unsaturated carboxylic acid or fatty acid with 14 to 30 carbon atoms. The at least one carboxylic acid may be contained in accordance with the invention in a quantity from 9 to 30 wt. %, preferably 10 to 25 wt. %, more preferably 11 to 22 wt. %, and in particular 12 to 16 wt. %, based on the total weight of the cleansing composition. With the use of the previously described quantities of partially and/or non-neutralized carboxylic acids b), a texture that is appealing visually and in a sensory manner and a high care property of the cleansing composition according to the invention are obtained.

Carboxylic acids b) preferred in accordance with the invention are myristic acid, coconut acid, palmitic acid, stearic acid, oleic acid, eladidc acid, petroselinic acid, linoleic acid, linolenic acid, elaeostearic acid, arachidic acid, gadoleic acid, behenic acid, erucic acid, lignoceric acid, cerotic acid, and technical mixtures thereof which for example occur in the event of the pressure-splitting of natural fats and oils, in the event of oxidation of aldehydes from Roelens oxosynthesis or the dimerization of unsaturated fatty acids. Carboxylic acids with 16 to 22 carbon atoms are particularly preferred. The above-mentioned carboxylic acids demonstrate a good regreasing behavior, such that a drying out of the skin and/or of the hair is avoided, even in the case of frequent application of the cleansing composition.

In this context, in accordance with a preferred embodiment of the present invention, stearic acid and/or palmitic acid can be used as carboxylic acid b).

The cleansing compositions according to the invention also contain non-ionic polymers c). In accordance with a preferred embodiment of the present invention water-soluble non-ionic polymers c) are used. Within the scope of the present invention the term "water-soluble" is to be understood to mean non-ionic polymers c) that in 1% concentration at 25° C. deliver solutions in water that are clear or translucent to the human eye.

Non-ionic polymers c) used in accordance with the invention correspond to formula (I)

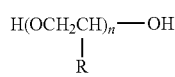

(I)

in which R represents a hydrogen atom or a methyl group, and n represents a whole number value from 1,360 to 99,000. Particularly preferred non-ionic polymers c) have a whole number value n from 1,360 to 97,000, more preferably from 1,360 to 94,000, and in particular from 1368 to 91,000.

Polyethylene glycols with mean molecular weights $M_w$ in the range from 600,000 to 10,000,000 daltons, preferably from 100,000 to 9,000,000 daltons, more preferably from 300,000 to 8,000,000 daltons, even more preferably from 500,000 to 7,000,000 daltons, and in particular from 600,000 to 4,000,000 daltons are particularly preferred. The mean molecular weight $M_w$, can be determined for example by gel permeation chromatography (GPC) with polystyrene as internal standard according to DIN 55672-3.

The non-ionic polymers c) can be used in the cleansing composition according to the invention in quantities from 0.005 to 5 wt. %, preferably from 0.01 to 4 wt. %, more preferably from 0.05 to 2 wt. %, and in particular from 0.1 to 1 wt. %, based on the total weight of the cleansing composition.

It has been found that these special non-ionic polymers c) significantly improve the foaming behavior of the cleansing compositions according to the invention and that a high a foam formation is attained even with high contents of partially and/or non-neutralized carboxylic acids, which act negatively on the foaming behavior. Furthermore, the high-molecular non-ionic polymers c) support the rheology of the cleansing compositions according to the invention and also the foaming properties thereof, in particular the fine porosity and creaminess of the foam, such that a mousse-like texture results. In addition, the use of the high-molecular non-ionic polymers c) leads to a high stability of the mousse-like texture of the cleansing compositions according to the invention, such that the cleansing compositions can be packaged, stored and marketed as a mousse. The use of propellant gases, which are harmful to the environment, in aerosol cans or complex packaging types, such as pump dispensers, can thus be avoided. Due to the use of the high-molecular non-ionic polymers c), the undesirable slimy feel of the foam, on the skin, which is experienced with many commercial products, can be avoided.

In accordance with a preferred embodiment of the present invention the cleansing compositions may contain an inorganic thickener. Within the scope of the present invention sheet silicates (polymeric, crystalline sodium disilicates) can be used as inorganic thickening agents. Particularly stable foams having outstanding foaming properties are obtained when magnesium aluminum silicates from the group of bentonites, in particular smectites, such as montmorillonite or hectorite, which may optionally also be suitably modified, are used as inorganic thickener. In addition, synthetic sheet silicates, such as the magnesium sheet silicate sold by Sud Chemie under the trade name Optigel can also be used.

Besides the above-mentioned constituents, the cleansing compositions may also now contain a series of further optional constituents. Further active ingredients which have additional cosmetic care properties are added to the cleansing compositions according to the invention in order to support the conditioning of the skin and/or the hair during the cleansing process. These include, in particular, cosmetically suitable oil components, plant extracts and/or humectants as further preferred optional components.

Oil components that are suitable in accordance with the invention can be selected from mineral, natural or synthetic oil components, such as petrolatum, paraffins, silicones, alcohols, fatty acid esters, natural oils of plant and animal origin and mixtures thereof. The oil components can be used in a quantity from 0.005 to 20 wt. %, preferably from 0.01 to 10 wt. %, particularly preferably from 0.05 to 5 wt. %, and in particular from 0.2 to 3 wt. %, based on the total weight of the cleansing composition and the total content of all oil components.

The term silicones is understood by a person skilled in the art to mean various structures of organosilicon compounds, which may be contained in the cleansing composition according to the invention in quantities from 0.01 to 3 wt. %, preferably from 0.05 to 2 wt. %, and in particular from 0.1 to 1 wt. %, based on the total weight of the cleansing composition.

The silicones can be particularly preferably selected from at least one representative of the group of organosilicon compounds, said group being formed from:
(i) polyalkylsiloxanes, polyarylsiloxanes, polyalkylarylsiloxanes, which are volatile or non-volatile, linear, branched, or cyclic, cross-linked or non-cross-linked;
(ii) polysiloxanes containing in their general structure one or more organofunctional groups selected from:
   a) substituted or unsubstituted aminated groups;
   b) (per)fluorinated groups;
   c) thiol groups;
   d) carboxylate groups;
   e) hydroxylated groups;
   f) alkxoylated groups;
   g) acyloxyalkyl groups;
   h) amphoteric groups;
   i) bisulfite groups;
   j) hydroxyacyl amino groups;
   k) carboxy groups;
   l) sulfonic acid groups; and
   m) sulfate or thiosulfate groups;
(iii) linear polysiloxane (A) polyoxyalkylene (B) block copolymers of the type $(A-B)_n$ with n>3;
(iv) grafted silicone polymers with non-silicon-containing, organic skeleton, which consist of an organic main chain which is formed from organic monomers containing no silicone, onto which, in the chain and optionally at least at one chain end, at least one polysiloxane macromer was grafted;
(v) grafted silicone polymers with a polysiloxane skeleton, onto which non-silicone-containing organic monomers have been grafted, having a polysiloxane main chain onto which, in the chain and optionally at least at one of the ends thereof, at least one organic macromer has been grafted, said macromer containing no silicone, such as the commercial product Abil B 8832 sold under the INCI name Bis-PEG/PPG-20/20 Dimethicone by Degussa;
(vi) or mixtures thereof In one embodiment of the present invention the conditioning agent is a conditioning silicone having a viscosity from 20,000 to 120,000 mPa·s, especially preferably from 40,000 to 80,000 mPa·s.

Here, the conditioning silicone is particularly preferably selected from dimethicones, amodimethicones or dimethiconols Saturated, mono- or polyunsaturated, branched or unbranched fatty alcohols with $C_6$-$C_{30}$, preferably $C_{10}$-$C_{22}$ and especially preferably $C_{12}$-$C_{22}$ carbon atoms can be used as fatty alcohols. In the context of the invention, decanol, octanol, octenol, dodecenol, decenol, octadienol, dodecadienol, decadienol, oleyl alcohol, erucic alcohol, ricinolyl alcohol, stearyl alcohol, isostearyl alcohol, cetyl alcohol, lauryl alcohol, myristyl alcohol, arachidyl alcohol, caprylic alcohol, capric alcohol, linoleyl alcohol, linolenyl alcohol and behenyl alcohol and the Guerbet alcohols thereof can be used by way of example, wherein this list is to be understood to be of an exemplary and non-limiting character. However, the fatty alcohols originate from preferably natural fatty acids with $C_6$-$C_{30}$ carbon atoms, wherein these can usually be assumed to have been obtained from the esters of the fatty acids by reduction. In accordance with the invention, fatty alcohol slices which are produced by reduction of naturally occurring triglycerides, such as beef tallow, palm oil, peanut oil, rapeseed oil, cotton seed oil, soybean oil, sunflower oil and linseed oil, or fatty acid esters produced from the transesterification products thereof with corresponding alcohols, and thus represent a mixture of different fatty alcohols, can also be used. Such substances can be purchased for example under the names Stenol®, for example Stenol® 1618 or Lanette®, for example Lanette® O or Lorol®, for example Lorol® C8, Lorol® C14, Lorol®, C18, Lorol® C8-18, HD Ocenol®, Crodacol®, for example Crodacol®, CS, Novol®, Eutanol® G, Guerbitol® 16, Guerbitol® 18, Guerbitol® 20, Isofol® 12, Isofol® 16, Isofol® 24, Isofol® 36, Isocarb® 12, Isocarb® 16 or Isocarb® 24. Of course, wool wax alcohols, as are available for purchase for example, under the names Corona®, White Swan®, Coronet® or Fluilan®, can also be used in accordance with the invention.

Fatty alcohols that are suitable in accordance with the invention are used in the cleansing composition in quantities from 0.01 to 3 wt. %, preferably in quantities from 0.05 to 2 wt. %, and in particular from 0.1 to 1 wt. %, based on the total weight of the cleansing composition.

In accordance with the invention, solid paraffins or isoparaffins, carnauba wax, beeswax, candelilla wax, ozokerite, ceresin, spermaceti, sunflower wax, fruit waxes such as apple wax or citrus wax, and micro waxes from PE or PP can be used as natural or synthetic wax. Such waxes are obtainable for example via the company. Kahl & Co., Trittau.

The natural and synthetic cosmetic oil bodies for example include:

Liquid paraffin oils, isoparaffin oils and synthetic hydrocarbons, and di-n-alkyl ethers with a total of 12 to 36 carbon atoms, in particular 12 to 24 carbon atoms, such as di-n-octyl ether, di-n-decyl ether, di-n-nonyl ether, di-n-undecyl ether, di-n-dodecyl ether, n-hexyl-n-octyl ether, n-octyl-n-decyl ether, n-decyl-n-undecyl ether, n-undecyl-n-dodecyl ether and n-hexyl-n-undecyl ether and di-tert-butyl ether, di-iso-pentyl ether, di-3-ethyldecylether, tert-butyl-n-octyl ether, isopentyl-n-octyl ether and 2-methyl-pentyl-n-octyl ether. The commercially available compounds 1,3-di(2-ethylhexyl)cyclohexane (Cetiol® S) and di-n-octyl ether (Cetiol® OE) may be preferred.

Ester oils. Ester oils are understood to be the esters of $C_6$-$C_{30}$ fatty acids with $C_2$-$C_{30}$ fatty alcohols. The monoesters of fatty acids with alcohols with 2 to 24 carbon atoms are preferred. Examples of used fatty acid moieties in the esters are caproic acid, caprylic acid, 2-ethyl hexanoic acid, capric acid, lauric acid, isotridecanoic, myristic acid, palmitic acid, palmitoleic, stearic, isostearic acid, oleic acid, elaidic acid, petroselinic acid, linoleic acid, linolenic acid, elaeostearic acid, arachidic acid, gadoleic, behenic acid and erucic acid, and technical mixtures thereof which occur for example in the event of the pressure-splitting of natural fats and oils, in the event of the oxidation of aldehydes from Roelens oxosynthesis or the dimerization of unsaturated fatty acids. Examples of the fatty alcohol components in the ester oils are isopropyl alcohol, caproic acid, caprylic acid, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol and brassidyl alcohol and technical mixtures thereof which occur for example in the event of the high-pressure hydrogenation of technical methyl esters based on fats and oils or aldehydes from Roelens oxosynthesis and as monomer fraction in the dimerization of unsaturated fatty alcohols. In accordance with the invention isopropyl myristate (Rilanit® IPM), isononanoic $C_{16-18}$ alkyl (Cetiol® SN), 2-ethylhexyl palmitate (Cegesoft® 24), stearic acid 2-ethylhexyl ester (Cetiol® 868), cetyl oleate, glycerol tricaprylate, coconut fatty alcohol caprinat/caprylate (Cetiol® LC), n-butyl stearate, oleyl eructae (Cetiol® J 600), isopropyl palmitate (Rilanit® IPP), oleyl oleate (Cetiol®), lauric acid hexyl ester (Cetiol® A), di-n-butyl adipate (Cetiol® B), myristyl myristate (Cetiol® MM), cetearyl isononanoate (Cetiol® SN) and oleic acid decyl ester (Cetiol® V) are particularly preferred.

Dicarboxylic acid esters, such as di-n-butyl adipate, di-(2-ethylhexyl) adipate, di-(2-ethylhexyl) succinate and di-isotridecylacelaat and diol esters, such as ethylene glycol dioleate, ethylene glycol di-isotridecanoate, propylene glycol di-(2-ethylhexanoate), propylene glycol diisostearate, propylene glycol di-pelargonate, butanediol diisostearate, neopentyl glycol dicaprylate.

Symmetrical, asymmetrical or cyclic esters of carbonic acid with fatty alcohols, glycerol carbonate or dicaprylyl carbonate (Cetiol® CC).

Trifatty acid esters of saturated and/or unsaturated linear and/or branched fatty acids with glycerol.

Fatty acid partial glycerides, i.e. monoglycerides, diglycerides and technical mixtures thereof. When using technical products, small amounts of triglycerides may also be contained due to production reasons. The partial glycerides preferably have the formula (II)

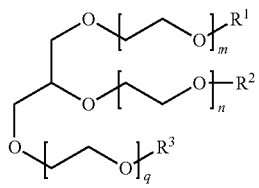

in which $R^2$ and $R^3$ each independently of one another represent hydrogen or a linear or branched, saturated and/or unsaturated acyl group with 6 to 22, preferably 12 to 18, carbon atoms, with the proviso that at least one of these groups is an acyl group and at least one of these groups is hydrogen. The sum (m+n+q) is 0 or a number from 1 to 100, preferably 0 or 5 to 25. Preferably, $R^1$ is an acyl group and $R^2$ and $R^3$ are hydrogen and the sum (m+n+q) is 0. Examples are mono- and/or diglycerides based on caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselinic acid, linoleic acid, linolenic acid, elaeostearic acid, arachidic acid, gadoleic acid, behenic acid and erucic acid and technical mixtures thereof. Oleic acid monoglycerides are preferably used.

In a particularly preferred embodiment of the invention a vegetable oil is used as oil component.

By way of example, amaranth seed oil, apricot kernel oil, argan oil, avocado oil, babassu oil, cotton seed oil, borage seed oil, camelina oil, safflower oil, peanut oil, pomegranate seed oil, grapefruit seed oil, hemp oil, rosehip seed oil, hazelnut oil, elderberry seed oil, blackcurrant seed oil, jojoba oil, cocoa butter, flaxseed oil, macadamia nut oil, corn oil, almond oil, manila oil, evening primrose oil, olive oil, palm oil, peach kernel oil, rapeseed oil, rice oil, sea buckthorn oil, sea buckthorn seed oil, sesame oil, shea butter, soybean oil, sunflower oil, grape seed oil, walnut oil or rosehip oil can be used as natural oils.

In accordance with the invention, avocado oil, apricot kernel oil, rosehip seed oil, jojoba oil, cocoa butter, almond oil, olive oil, peach kernel oil, shea butter, sunflower oil and grapeseed oil are particularly preferred.

The oils are used in the cleansing composition according to the invention in quantities from 0.01 to 3 wt. %, preferably from 0.05 to 2.5 wt. %, and in particular in quantities from 0.1 to 2 wt. %, based on the total weight of the cleansing composition.

Plant extracts that are suitable in accordance with the invention to be understood to mean extracts which can be produced from all parts of a plant.

These extracts are usually produced by extraction of the entire plant. However, it may also be preferred in individual cases to produce the extracts exclusively from flowers and/or leaves of the plant.

In accordance with the invention, the extracts from green tea, white tea, oak bark, nettle, hamamelis, hops, chamomile, burdock, horsetail, hawthorn, linden blossom, lychee, almond, aloe vera, pine needle, horse chestnut, sandalwood, juniper, coconut, mango, apricot, lemon, wheat, kiwi, melon, orange, grapefruit, sage, rosemary, birch, mallow, lady's smock, wild thyme, yarrow, thyme, lemon balm, restharrow, coltsfoot, hibiscus, ginseng, ginger root, echinacea purpurea, olea europea, foeniculum vulgaris and apim graveolens are especially preferred.

Water, alcohols and mixtures thereof can be used as extractants for producing the specified plant extracts. Among the alcohols, lower alcohols such as ethanol and isopropanol, but especially polyhydric alcohols such as ethylene glycol and propylene glycol are preferred, both as sole extractant or in a mixture with water. Plant extracts based on water/propylene glycol in the ratio 1:10 to 10:1 have proven to be particularly suitable.

The plant extracts can be used in accordance with the invention both in pure and in diluted form. If they are used in diluted form, they usually contain approximately 2 to 80 wt. % active substance and, as a solvent, the extractant or extractant mixture used to obtain them.

Additionally, it may prove advantageous to add humectants and/or penetration auxiliaries and/or swelling agents to the cleansing compositions according to the invention. These auxiliaries provide better penetration of active ingredients into the keratin fibers or help swell the keratin fibers. These include, for example, urea and urea derivatives, guanidine and its derivatives, arginine and its derivatives, water glass, imidazole and derivatives thereof, histidine and its derivatives, benzyl alcohol, glycerol, glycol and glycol ether, propylene glycol and propylene glycol ether, such as propylene glycol monoethyl ethers, carbonates, bicarbonates, diols and triols, and in particular 1,2-diols and 1,3-diols, such as 1,2-propanediol, 1,2-pentanediol, 1,2-hexanediol, 1,2-dodecanediol, 1,3-propanediol, 1,6-hexanediol, 1,5-pentanediol, 1,4-butanediol. Glycerol is particularly suitable in accordance with the invention.

The humectants are used in the cleansing composition according to the invention in quantities from 0.01 to 10 wt. %, preferably in quantities from 0.05 to 5 wt. %, and particularly in quantities from 0.1 to 3 wt. %, based on the total weight of the cleansing composition.

Besides the aforementioned mandatory components according to the invention and the optional, but preferred further components, the cleansing compositions according to the invention may contain further substances which condition the skin and/or the hair or improve the application properties of the agent.

Cationic polymers are included in accordance with the invention with the further conditioning components. Cationic polymers that are suitable in accordance with the invention are to be understood to mean polymers which have in the main and/or side chain "temporarily cationic" or "permanently cationic" groups. In accordance with the invention, "permanently cationic" polymers are polymers which have a cationic group irrespective of the pH value of the agent. These are generally polymers which contain a quaternary nitrogen atom, for example in the form of an ammonium group.

Preferred cationic groups contain quaternary ammonium groups. In particular, polymers in which the quaternary ammonium group is bonded via a $C_{1-4}$ hydrocarbon group to a polymer main chain constructed from acrylic acid, methacrylic acid or derivatives thereof have proven to be particularly suitable.

Particularly preferred cationic polymers are homopolymers of the general formula (VI),

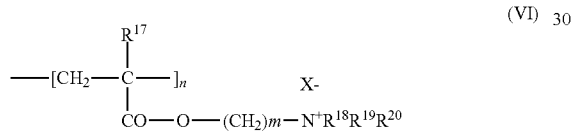

in which $R^{17}$=—H or —$CH_3$, $R^{18}$, $R^{19}$ and $R^{20}$ independently of one another are selected from $C_{1-4}$ alkyl, alkenyl or hydroxyalkyl groups, m=1, 2, 3 or 4, n is a natural number and $X^-$ is a physiologically acceptable organic or inorganic anion, and copolymers, consisting substantially of the monomer units specified in formula (VI) and non-ionogenic monomer units.

Within the scope of the previously mentioned polymers, those for which at least one of the following conditions applies are preferred in accordance with the invention:

$R^{17}$ represents a methyl group $R^{18}$, $R^{19}$ and $R^{20}$ represent methyl groups m has the value 2.

By way of example, halide ions, sulfate ions, phosphate ions, methosulfate ions and organic ions such as lactate, citrate, tartrate and acetate ions can be considered as physiologically acceptable counterions $X^-$. Halide ions, in particular chloride, are preferred.

Homopolymers or copolymers that derive from the formula (VI) are suitable in accordance with the invention, for example the cationic polymers available commercially under the trade names Salcare® SC 95, Salcare® SC 96 and Salcare® SC 92.

Further preferred cationic polymers include, for example quaternized cellulose derivatives, such as those commercially available under the names Celquat® and Polymer JR®. The compounds Celquat® H 100, Celquat® L 200 and Polymer JR® 400 are preferred quaternized cellulose derivatives, hydrophobically modified cellulose derivatives, such as the cationic polymers sold under the trade name Soft-Cat®, cationic alkylpolyglycosides, cationized honey, for example the commercial product Honeyquat® 50, cationic guar derivatives, in particular the products sold under the trade names Cosmedia®Guar and Jaguar®, polysiloxanes with quaternary groups, such as the commercially available products Q2-7224 (manufacturer: Dow Corning; a stabilized trimethylsilylamodimethicone), Dow Corning® 929 Emulsion (containing a hydroxylamino-modified silicone, which is also known as amodimethicone), SM-2059 (Manufacturer: General Electric), SLM 55067 (manufacturer: Wacker) and Abil®-Quat 3270 and 3272 (manufacturer: Th. Goldschmidt; diquaternary polydimethylsiloxanes, Quaternium-80), polymeric dimethyldiallylammonium salts and copolymers thereof with esters and amides of acrylic acid and methacrylic acid. The products commercially available under the names Merquat® 100 (poly(dimethyldiallylammonium chloride)) and Merquat® 550 (dimethyldiallylammonium chloride acrylamide copolymer) are examples of such cationic polymers, copolymers of vinylpyrrolidone with quaternized derivatives of dialkylaminoalkyl acrylate and methacrylate, such as vinylpyrrolidone-dimethylaminoethyl methacrylate copolymers quaternized with diethyl sulfate. Such compounds are commercially available under the names Gafquat® 734 and Gafquat® 755, vinylpyrrolidone vinylimidazoliummethochloride copolymers, such as those offered under the names Luviquat® FC 370, FC 550, FC 905 and HM 552, quaternized polyvinyl alcohol, and also the polymers with quaternary nitrogen atoms in the polymer main chain known under the names Polyquaternium 2, Polyquaternium 17, Polyquaternium 18 and Polyquaternium 27.

The polymers known under the names Polyquaternium 24 (commercial product, for example Quatrisoft® LM 200) can be used equally as cationic polymers. The copolymers of vinylpyrrolidone as are available as commercial products Copolymer 845 (manufacturer: ISP), Gaffix® VC 713 (manufacturer: ISP), Gafquat® ASCP 1011, Gafquat® HS 110 Luviquat® 8155 and Luviquat® MS 370 likewise can be used in accordance with the invention.

Other cationic polymers according to the invention are what are known as "temporarily cationic" polymers. These polymers usually contain an amino group which is present as a quaternary ammonium group and thus cationic at certain pH values. Preference is given, for example, to chitosan and derivatives thereof, as are freely commercially available, for example, under the trade names Hydagen® CMF, Hydagen® HCMF, Kytamer® PC and Chitolam® NB/101. Chitosans are deacetylated chitines, which are commercially available in different degrees of deacetylation and varying degrees of degradation (molecular weights).

In a particularly preferred embodiment of the invention, the cleansing compositions according to the invention contain at least one cationic polymer, which is selected from the group of cationic cellulosic derivatives, cationic guar derivatives and/or Polyquaternium-7 (Merquat 550), Polyquaternium-6, Polyquaternium-10 and/or Polyquaternium-67 (SoftCat® polymers), in order to increase the skin conditioning.

The cationic polymer(s) is (are) present in the cleansing composition according to the invention in quantities from 0.1 to 5 wt. %, based on the total weight of the cleansing composition. Quantities from 0.2 to 3 wt. %, particularly from 0.5 to 2 wt. %, based on the total weight of the cleansing composition, are particularly preferred.

The cleansing compositions according to the invention are particularly suitable as cosmetic compositions for the cleansing of the skin and/or the hair and can be present for example in the form of hair shampoo, shower gel, bath soak, washing gel, face cleanser, handwash agent, and/or foam bath product. They have excellent foaming properties and a mousse-like texture and provide excellent care on account of the high proportion of partially and/or non-neutralized carboxylic acids, such that there is no drying of the skin even in the event of frequent application.

Depending on its purpose, the cleansing composition according to the invention, besides the aforementioned mandatory and preferred optional components, may also contain further active ingredients, auxiliaries and additives, which will be described hereinafter.

Cationic surfactants of the quaternary ammonium compound, esterquat and amidoamine type can be used in accordance with the invention. Preferred quaternary ammonium compounds are ammonium halides, particularly chlorides and bromides, such as alkyltrimethyl ammonium chlorides, dialkyldimethyl ammonium chlorides and trialkylmethyl ammonium chlorides, for example cetyltrimethyl ammonium chloride, stearyl trimethyl ammonium chloride, distearyldimethyl ammonium chloride, lauryldimethyl ammonium chloride, lauryldimethylbenzyl ammonium chloride and tricetylmethylammonium chloride, as well as imidazolium compounds known under the INCI names Quaternium-27 and Quaternium-83. The long alkyl chains of the abovementioned surfactants preferably have 10 to 18 carbon atoms.

Esterquats are known substances which contain at least one ester function and at least one quaternary ammonium group as structural element. Preferred esterquats are quaternized ester salts of carboxylic acids with triethanolamine, quaternized ester salts of carboxylic acids with diethanolalkylamines and quaternized ester salts of carboxylic acids with 1,2-dihydroxypropyl dialkyl amines. Such products are sold, for example, under the trade marks Stepantex®, Dehyquart® and Armocare®. The products Armocare® VGH-70, an N,N-bis(2-palmitoyloxyethyl)dimethyl ammonium chloride, and Dehyquart® F-75, Dehyquart® C-4046, Dehyquart® L80 and Dehyquart® AU-35 are examples of such esterquats.

Alkylamidoamines are usually prepared by amidation of natural or synthetic fatty acids and fatty acid slices with dialkylaminoamines. A compound from this group of substances that is particularly suitable in accordance with the invention is the stearamidopropyl dimethylamine commercially available under the name Tegoamid® S 18.

The cationic surfactants are preferably present in quantities from 0.05 to 10 wt. %, based on the total weight of the cleansing composition used. Quantities from 0.1 to 5 wt. %, based on the total weight of the cleansing composition are particularly preferred.

In a further preferred embodiment the effect of the cleansing compositions according to the invention can be enhanced by emulsifiers. Such emulsifiers are, for example addition products from 4 to 30 mol ethylene oxide and/or 0 to 5 mol propylene oxide onto linear fatty alcohols with 8 to 22 carbon atoms, onto fatty acids with 12 to 22 carbon atoms and onto alkylphenols with 8 to 15 carbon atoms in the alkyl group, $C_{12}$-$C_{22}$ fatty acid monoesters and diesters of addition products from 1 to 30 mol ethylene oxide onto polyols with 3 to 6 carbon atoms, in particular onto glycerol, ethylene oxide and polyglycerol addition products with methyl glucoside fatty acid esters, fatty acid alkanolamides and fatty acid glucamides, $C_8$-$C_{22}$ alkyl mono- and oligoglycosides and ethoxylated analogs thereof, wherein degrees of oligomerization from 1.1 to 5, in particular 1.2 to 2.0, and glucose are preferred as the sugar component, mixtures of alkyl (oligo) glucosides and fatty alcohols, for example the commercially available product Montanov® 68, addition products from 5 to 60 mol ethylene oxide onto castor oil and hydrogenated castor oil, partial esters of polyols with 3-6 carbon atoms with saturated fatty acids with 8 to 22 carbon atoms, Sterols. Sterols are to be understood to be a group of steroids which carry a hydroxyl group at carbon atom 3 of the steroid backbone and are formed both from animal tissue (zoosterols) and from vegetable fats (phytosterols). Examples of zoosterols are cholesterol and lanosterol. Examples of suitable phytosterols are ergosterol, stigmasterol and sitosterol. Sterols known as mycosterols are also isolated from fungi and yeasts.

Phospholipids. These are understood to be primarily the glucose phospholipids, obtained for example as lecithins or phosphatidylcholines from, for example, egg yolk or plant seeds (for example soybeans).

Fatty acid esters of sugars and sugar alcohols such as sorbitol, polyglycerol and polyglycerol derivatives such as polyglycerol poly-12-hydroxy stearate (commercial product Dehymuls® PGPH), linear and branched fatty acids containing 8 to 30 carbon atoms and the Na, K, ammonium, Ca, Mg and Zn salts thereof, monoesters and/or mixtures of monoesters and diesters of glycerol with branched or linear, saturated or unsaturated carboxylic acids having a carbon chain length from 8 to 24, preferably from 10 to 18 and particularly from 12 to 16, a degree of ethoxylation from 1 to 20, preferably from 2 to 17, particularly preferably from 4 to 13, and in particular from 6 to 10. In accordance with the invention, the ethoxylated glyceryl oleates and glyceryl cocoates and particularly preferably PEG-7 glyceryl cocoate, as obtainable commercially for example under the name Tegosoft® GC or Cetiol® HE, are preferred in accordance with the invention.

The emulsifiers are used preferably in quantities from 0.1 to 25 wt. %, in particular 0.5 to 15 wt. %, based on the total weight of the cleansing composition.

In principle, non-ionic emulsifiers can be used having an HLB value from 8 to 18. Non-ionic emulsifiers having an HLB value from 10 to 15 may be preferred in accordance with the invention.

In a further embodiment of the invention the cleansing compositions according to the invention may additionally contain protein hydrolyzates and/or derivatives thereof in order to further support the skin and hair care effect of said compositions. Protein hydrolyzates are product mixtures obtained by acidic, alkaline or enzymatically catalyzed degradation of proteins.

Protein hydrolyzates of plant and animal origin may be used in accordance with the invention.

Animal protein hydrolyzates include, for example, elastin, collagen, keratin, silk and milk protein hydrolyzates, which can also be in the form of salts. Such products are sold for example under the trade marks Dehylan® (Cognis), Promois® (Interorgana), Collapuron® (Cognis), Nutrilan® (Cognis), Gelita-Sol® (German gelatin factories Stoess & Co), Lexein® (Inolex) and Kerasol® (Croda).

Protein hydrolyzates of plant origin, for example soy, almond, rice, pea, potato and wheat protein hydrolyzates, are preferred in accordance with the invention. Such products are available for example under the trade marks Gluadin® (Cognis), DiaMin® (Diamalt)®, Lexein® (Inolex) and Crotein® (Croda).

Although the use of protein hydrolyzates as such is preferred, amino acid mixtures obtained in other ways or individual amino acids such as arginine, lysine, histidine or pyroglutamic acid can also be used instead if necessary. It is also possible to use derivatives of protein hydrolyzates, for example in the form of the fatty acid condensation products thereof. Such products are sold for example under the names Lamepon® (Cognis), Gluadin® (Cognis), Lexein® (Inolex), Crolastin® (Croda) or Crotein® (Croda).

Cationized protein hydrolyzates, wherein the underlying protein hydrolyzate may originate from animals, for example from collagen, milk or keratin, from plants, such as wheat, corn, rice, potatoes, soy or almonds, from marine life forms, for example from fish collagen or algae, or from protein hydrolyzates derived on the basis of biotechnology, can also be used in accordance with the invention. The protein hydrolyzates forming the basis of the cationic derivatives according to the invention can be obtained from the corresponding proteins by a chemical, in particular alkaline or acidic hydrolysis, by an enzymatic hydrolysis and/or by a combination of both hydrolysis types. The hydrolysis of proteins usually yields a protein hydrolyzate with a molecular weight distribution of about 100 daltons up to several thousand daltons. Preference is given to those cationic protein hydrolyzates of which the underlying protein fraction has a molecular weight from 100 to 25,000 daltons, preferably 250 to 5,000 daltons. Quaternized amino acids and mixtures thereof are also to be understood as cationic protein hydrolyzates. The quaternization of the protein hydrolyzates or amino acids is often performed by means of quaternary ammonium salts such as N,N-dimethyl-N-(n-alkyl)-N-(2-hydroxy-3-chloro-n-propyl) ammonium halides. The cationic protein hydrolyzates can also be further derivatized. Typical examples of the cationic protein hydrolyzates and derivatives according to the invention are the products specified under the INCI names in the "International Cosmetic Ingredient Dictionary and Handbook" (seventh edition 1997 The Cosmetic, Toiletry, and Fragrance Association 1101 17th Street, N.W., Suite 300, Washington, D.C. 20036-4702) and commercially available: Cocodimonium Hydroxypropyl Hydrolyzed Collagen, Cocodimopnium Hydroxypropyl Hydrolyzed Casein, Cocodimonium Hydroxypropyl Hydrolyzed Collagen, Hydroxypropyl Hydrolyzed Hair Keratin, Cocodimonium Hydroxypropyl Hydrolyzed Keratin, Cocodimonium Hydroxypropyl, Hydrolyzed Rice Protein, Cocodimonium Hydroxypropyl Hydrolyzed Silk, Cocodimonium Hydroxypropyl Hydrolyzed Soy Protein, Cocodimonium Hydroxypropyl Hydrolyzed Wheat Protein, Cocodimonium Hydroxypropyl Silk Amino Acids, Hydroxypropyl Arginine Lauryl/Myristyl Ether HCl, Hydroxypropyltrimonium Gelatin, Hydroxypropyltrimonium Hydrolyzed Casein, Hydroxypropyltrimonium Hydrolyzed Collagen, Hydroxypropyltrimonium Hydrolyzed Conchiolin Protein, Hydroxypropyltrimonium Hydrolyzed keratin, Hydroxypropyltrimonium Hydrolyzed Rice Bran Protein, Hydroxyproypltrimonium Hydrolyzed Silk, Hydroxypropyltrimonium Hydrolyzed Soy Protein, Hydroxypropyl Hydrolyzed Vegetable Protein, Hydroxypropyltrimonium Hydrolyzed Wheat Protein, Hydroxypropyltrimonium Hydrolyzed Wheat Protein/Siloxysilicate, Laurdimonium Hydroxypropyl Hydrolyzed Soy Protein, Laurdimonium Hydroxypropyl Hydrolyzed Wheat Protein/Siloxysilicate, Lauryldimonium Hydroxypropyl Hydrolyzed Casein, Lauryldimonium Hydroxypropyl Hydrolyzed Collagen, Lauryldimonium Hydroxypropyl Hydrolyzed Keratin, Lauryldimonium Hydroxypropyl Hydrolyzed Silk, Lauryldimonium Hydroxypropyl Hydrolyzed Soy Protein, Steardimonium Hydroxypropyl Hydrolyzed Casein, Steardimonium Hydroxypropyl Hydrolyzed Collagen, Steardimonium Hydroxypropyl Hydrolyzed Keratin, Steardimonium Hydroxypropyl Hydrolyzed Rice Protein, Steardimonium Hydroxypropyl Hydrolyzed Silk, Steardimonium Hydroxypropyl Hydrolyzed Soy Protein, Steardimonium Hydroxypropyl Hydrolyzed Vegetable Protein, Steardimonium Hydroxypropyl Hydrolyzed Wheat Protein, Steartrimonium Hydroxyethyl Hydrolyzed Collagen, Quaternium-76, Hydrolyzed Collagen, Quaternium-79 Hydrolyzed Silk, Quaternium-79 Hydrolyzed Soy Protein, Quaternium-79 Hydrolyzed Wheat Protein. The cationic protein hydrolyzates and derivatives based on plants are especially preferred.

The protein hydrolyzates and derivatives thereof are preferably used in quantities from 0.01 to 10 wt. %, based on the total weight of the cleansing composition. Quantities from 0.1 to 5 wt. %, particularly from 0.1 to 3 wt. %, based on the total weight of the cleansing composition are especially preferred.

The combination of the cleansing composition according to the invention with vitamins, pro-vitamins and vitamin precursors and derivatives thereof has likewise proven to be advantageous.

In this case, vitamins, pro-vitamins and vitamin precursors which are commonly associated with the groups A, B, C, E, F, and H are preferred in accordance with the invention.

The group of substances designated as vitamin A includes retinol (vitamin $A_1$) and 3,4-didehydroretinol (vitamin $A_2$). The β-carotene is the provitamin of retinol. Vitamin A acid and esters thereof, vitamin A aldehyde and vitamin A alcohol and esters thereof, such as palmitate and acetate, can be considered for example as vitamin A components in accordance with the invention. The vitamin A component is preferably used in quantities from 0.05 to 1 wt. %, based on the total weight of the cleansing composition.

The vitamin B group or the vitamin B complex include, inter alia

Vitamin $B_1$ (thiamine)

Vitamin $B_2$ (riboflavin)

Vitamin $B_3$. The compounds nicotinic acid and nicotinamide (niacinamide) are often included under this name. In accordance with the invention, nicotinic acid amide is preferred, which is preferably used in quantities from 0.05 to 1 wt. %, based on the total weight of the cleansing composition.

Vitamin $B_5$ (pantothenic acid and panthenol). Within this group, panthenol is preferably used. Derivatives of panthenol that can be used in accordance with the invention are in particular the esters and ethers of panthenol and cationically derivatized panthenols. Individual representatives are, for example, panthenol triacetate, panthenol monoethyl ether, and the monoacetate thereof, and the panthenol cationic derivatives disclosed in WO 92/13829. The specified compounds of the vitamin $B_5$ type are preferably used in quantities from 0.05 to 10 wt. %, based on the total weight of the cleansing composition. Quantities from 0.1 to 5 wt. %, based on the total weight of the cleansing composition, are particularly preferred.

Vitamin $B_6$ (pyridoxine and pyridoxamine and pyridoxal).

Vitamin C (ascorbic acid). The usual amount used of vitamin C is from 0.1 to 3 wt. %, based on the total weight of the cleansing composition. The use in the form of the palmitic acid ester, the glucosides or phosphates may be preferred. The use in combination with tocopherols may likewise be preferred.

Vitamin E (tocopherols, in particular α-tocopherol). Tocopherol and its derivatives, including in particular the esters such as the acetate, nicotinate, phosphate and succinate, are preferably used in accordance with the invention in quantities from 0.05 to 1 wt. %, based on the total weight of the cleansing composition.

Vitamin F. The term "vitamin F" is usually understood to mean essential carboxylic acids, especially linoleic acid, linolenic acid and arachidonic acid.

Vitamin H. The compound (3aS,4S,6aR)-2-oxohexahydrothienol[3,4-d]imidazole-4 valeric acid is referred to as vitamin H, for which in the meantime the trivial name Biotin has become established. Biotin is preferably used in quantities from 0.0001 to 1.0 wt. %, particularly in quantities from 0.001 to 0.01 wt. %, based on the total weight of the cleansing composition.

The use of vitamins, pro-vitamins and vitamin precursors from groups A, B, E and H is particularly preferred in accordance with the invention. Panthenol and its derivatives as well as nicotinamide and biotin are particularly preferred.

Furthermore, a UV filter can be used additionally in a preferred embodiment of the invention. The UV filters to be used in accordance with the invention are not generally limited in terms of their structure and their physical properties. Rather, all UV filters usable in the cosmetic field of which the absorption maximum lies in the UVA (315-400 nm) range, in the UVB (280-315 nm) range, or in the UVC (<280 nm) range are suitable. UV-filters having an absorption maximum in the UVB range, in particular in the range of about 280 to about 300 nm, are particularly preferred.

The UV filters can for example be selected from substituted benzophenones, p-aminobenzoic acid esters, diphenylacrylates, cinnamates, salicylates, benzimidazoles and o-aminobenzoic acid esters.

In accordance with a further embodiment of the invention, UV filters which have a cationic group, in particular a quaternary ammonium group, are preferred.

Two preferred UV filters having cationic groups are the compounds cinnamic acid amidopropyl trimethyl ammonium chloride (Incroquat® UV-283) and dodecyl dimethyl aminobenzamido propyldimethyl ammonium tosylate (Escalol® HP 610), available as commercial products.

The UV filter(s) is/are usually used in quantities from 0.1 to 5 wt. %, based on the total weight of the cleansing composition. Quantities from 0.4 to 2.5 wt. %, based on the total weight of the cleansing composition, are preferable.

Regarding the type of cosmetic cleansing compositions according to the invention, there are no restrictions in principle. Suitable formulations of these compositions for example include creams, lotions, solutions, water, emulsions such as W/O, O/W, PIT emulsions (emulsions according to the teaching of phase inversion, called PIT), microemulsions and multiple emulsions, rough, unstable, monophase or multiphase shaking mixtures, and gels.

The cleansing compositions according to the invention are characterized not only by the excellent cleansing, caring and foaming properties, but are further distinguished by their application- and production-friendly rheology and viscosity.

For this purpose, they have a viscosity in the range of 5,000 mPas to 15,000 mPas, preferably from 6,000 mPas to 12,000 mPas, and in particular from 7,500 mPas to 10,500 mPas (measured in each case with a Haake viscometer Viscotester VT550; 20° C., measuring device cylinder MK-2; shear rate 8/sec).

In addition to the components mandatory in accordance with the invention and the other, above-mentioned preferred components, all further components known to a person skilled in the art for such cosmetic compositions can be used in principle.

Other active substances, auxiliaries and additives include, for example:

thickeners such as gelatins or plant gums, such as agar-agar, guar gum, alginates, xanthan gum, gum arabic, karaya gum, locust bean flour, linseed gums, dextrans, cellulose derivatives, such as methylcellulose, hydroxyalkylcellulose and carboxymethylcellulose, starch fractions and derivatives such as amylose, amylopectin and dextrins, fully synthetic hydrocolloids, such as polyvinyl alcohol, structuring agents such as maleic acid and lactic acid, solvents and solubilizers such as ethanol, isopropanol, ethylene glycol, propylene glycol, glycerol and diethylene glycol, fiber-structure-improving active ingredients, particularly mono-, di- and oligosaccharides such as glucose, galactose, fructose, levulose and lactose, dyes for coloring the agent, other substances for adjusting the pH value, such as α- and β-hydroxycarboxylic acids, active ingredients such as allantoin and bisabolol, complexing agents such as EDTA, NTA, β-alanine diacetic acid and phosphonic acids, ceramides. Ceramides are understood to be N-acylsphingosine (fatty acid amides of sphingosine) or synthetic analogues of such lipids (what are known as pseudoceramides), opacifiers, such as latex, styrene/PVP and styrene/acrylamide copolymers, pearlescent agents such as ethylene glycol mono- and distearate and PEG-3 distearate, pigments, propellants, such as propane-butane mixtures, $N_2O$, dimethyl ether, $CO_2$ and air, viscosity modifiers such as salts (NaCl).

The pH value of the cleansing compositions according to the inventions lies ideally in a range that is gentle on the skin from approximately 4 to 6, in particular in a range from 4.5 to 5.5.

In accordance with a further embodiment of the present invention the cleansing composition according to the invention may also contain a gas. Here, the gas may be selected from the group of air, argon, nitrogen, propane, butane, $N_2O$, dimethylether, $CO_2$, and mixtures thereof. In accordance with the invention, air or a mixture of air and propellant gases, such as propane and/or butane, is preferably used as gas.

In this context, the quantity of gas in the cleansing composition may be from 5 to 80 wt. %, preferably from 5 to 60 wt. %, more preferably from 5 to 40 wt. %, and in particular from 5 to 20 wt. %, based on the total weight of the cleansing composition. The quantity of the gas enclosed in the cleansing composition is given from the difference in weight of an identical volume of a cleansing composition with and without enclosed gas.

A second subject of the invention is the use of the previously described cleansing compositions according to the invention for cleansing and/or care of skin and hair. With regard to the use of the cleansing composition according to the invention, that mentioned with respect to the cleansing compositions according to the invention applies mutatis mutandis.

The following examples explain the invention, without however limiting it thereto.

EXAMPLES

The following cleansing compositions were produced, wherein all numerical values in the following tables 1 and 2, unless specified otherwise, correspond to the quantity of the respective raw material in wt. %:

TABLE 1 cleansing compositions according to the invention

| Raw material | Formulations | | | | | | | | |
|---|---|---|---|---|---|---|---|---|---|
| | I | II | III | IV | V | VI | VII | VIII | IX |
| Fatty alcohol polyglycol ether sulfate (C12-14), 2EO, 70% AS | 12 | 12 | 12 | | 12 | 12 | 12 | 12 | |
| Sodium lauryl sulfate AS | | | | 10 | | | | | |
| Disodiumlaurethsulfosuccinate 40% AS | | | | | | | | | 30 |
| Coconut amidopropylbetaine 40% AS | 8 | 8 | | 8 | 8 | 8 | 8 | 8 | 8 |
| Plantacare ® 818UP | | | 6 | | | | | | |
| Polyox ® WSR-301 | 0.1 | | | | | | 0.1 | | |
| Polyox ® WSR N-12K | | 0.1 | 0.1 | 0.1 | | | | | |
| Polyox ® WSR N-60K | | | | | 0.1 | | | | |
| Polyox ® WSR-205 | | | | | | 0.1 | | 0.1 | 0.1 |
| Cutina ® FS 45 | 15 | 15 | 15 | | 15 | 15 | 15 | 15 | 15 |
| Stearic acid | | | | 15 | | | | | |
| Isopropylpalmitate | 0.5 | 0.5 | 0.5 | | 0.5 | | | | |
| Isopropylmyristate | | | | | | 0.5 | | 0.5 | 0.5 |
| PEG-40 stearate | 0.5 | 0.5 | 0.5 | | 0.5 | 0.5 | | | |
| Cetiol ® HE | | | | | | | | 0.5 | 0.5 |
| Sodium benzoate | 0.4 | 0.4 | 0.4 | 0.4 | 0.4 | 0.4 | 0.4 | 0.4 | 0.4 |
| Citric acid | 0.25 | 0.25 | 0.25 | 0.25 | 0.25 | 0.25 | 0.25 | 0.25 | 0.25 |
| Sodium hydroxide 50% | 0.117 | 0.117 | 0.117 | 0.117 | 0.117 | 0.117 | 0.117 | 0.117 | 0.117 |
| Water | to 100 | to 100 | to 100 | to 100 | to 100 | to 100 | to 100 | to 100 | to 100 |

TABLE 2 cleansing compositions not according to the invention

| Raw material | Formulations | |
|---|---|---|
| | X | XI |
| Fatty alcohol polyglycol ether sulfate (C12-14), 2EO, 70% AS | 12 | 12 |
| Coconut amidopropylbetaine 40% AS | 8 | 8 |
| Cocomonoethanolamide | 2 | |
| Polymer JR 400 ® | | 2 |
| Cutina ® FS 45 | 15 | 15 |
| Isopropylpalmitate | 0.5 | 0.5 |
| PEG-40 stearate | 0.5 | 0.5 |
| Sodium benzoate | 0.4 | 0.4 |
| Citric acid | 0.25 | 0.25 |
| Sodium hydroxide 50% | 0.117 | 0.117 |
| Water | to 100 | to 100 |

The following commercial products were used:
Cocomonoethanolamide: INCI name: Cocamide MEA; Cognis
Cetiol® HE: INCI name: PEG-7 Glyceryl Cocoate; Cognis
Plantacare® 818UP: INCI name: Coco-glucoside, approximately 50% active substance; Cognis
Polymer JR 400®: INCI name: Polyquaternium-10, UNION CARBIDE
Cutina® FS 45: INCI name: Stearic Acid (and) Palmitic Acid, Cognis
Polyox® WSR-301: INCI name: PEG-90M, Dow Chemical Company
Polyox® WSR N-12K: INCI name: PEG-23M, Dow Chemical Company
Polyox® WSR N-60K: INCI name: PEG-45M, Dow Chemical Company
Polyox® WSR-205: INCI name: PEG-14M, Dow Chemical Company The cleansing compositions I to XI were produced in accordance with the following general rule:

The washing raw materials as well as the bulk of the water are heated to 70° C. to 80° C. and stirred until homogeneous. The thickeners pre-swollen in warm water and polymeric care ingredients were then added, where necessary. Once all ingredients had been added, a gassing with gas under cooling and stirring at 25° C. can be performed optionally. If no gassing is provided the mixture is cooled with stirring to 25° C. The preservative and, where appropriate, perfume oils mixed with a solubilizer, are added only at a temperature of 35° C. Once the cleansing composition has been cooled, the pH value is adjusted using citric acid.

Results:

The cleansing compositions according to the invention I to XI (see table 1) result in a visually appealing mousse-like texture and have excellent foaming properties in respect of foamability, spreadability, foam volume, pore size, creaminess, strength, stability and rinse-off capability.

The use of cationic polymers used in the prior art to increase foaming (cleansing compositions X and XI not according to the invention, see table 2) results in a significantly impaired foam formation, such that no mousse-like texture is obtained. Furthermore, the foam has an extremely low stability.

The foam properties of the cleansing compositions I to IX according to the invention were perceived as improved by a team of experts in a blind test compared with the cleansing compositions not according to the invention, which are based on cationic polymers.

The cleansing of the skin with cleansing compositions I to IX according to the invention led to effectively cleansed skin, which felt soft and nourished on account of the high proportion of non- and/or partially neutralized fatty acids.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A cosmetic, mousse-like cleansing composition, comprising:
    a) 0.1 to 30 wt. %, based on the total weight of the cleansing composition, of a surfactant selected from the group consisting of an anionic surfactant, a non-ionic surfactant, zwitterionic surfactant, or mixtures thereof,
    b) a carboxylic acid selected from the group consisting of stearic acid, palmitic acid, and mixtures thereof, in an amount from 9 to 30 wt. % based on the total weight of the cleansing composition, and
    c) at least one non-ionic polymer comprising a polyethylene glycol with a mean molecular weight of 600,000 to 4,000,000 daltons wherein the non-ionic polymer c) is included in a quantity from 0.1 to 1 wt. % based on the total weight of the cleansing composition,
    d) 0.01 to 3 wt. % of one or more naturally derived fatty alcohols with $C_6$-$C_{30}$ carbon atoms, and
        wherein the cosmetic cleansing composition does not contain a cationic polymer or a propellant, has a viscosity of 5,000 mPas to 15,000 mPas and is a foamed mousse.

2. The cleansing composition as claimed in claim 1, wherein at least one anionic and at least one non-ionic and/or zwitterionic surfactant is included, and wherein a weight ratio of the anionic surfactant(s) to the non-ionic and/or zwitterionic surfactant(s) is 3:1 to 1:2.

3. The cleansing composition as claimed in claim 1, wherein the anionic surfactant is included in a quantity from 0.3 to 30 wt. % based on the total weight of the cleansing composition.

4. The cleansing composition as claimed in claim 1, wherein the non-ionic and/or zwitterionic surfactant is contained in a quantity of 0.1 to 20 wt. % based on the total weight of the cleansing composition.

5. The cleansing composition as claimed in claim 1, wherein the at least one anionic surfactant is selected from the group consisting of alkyl polyglycol ether sulfates, alkyl sulfates, and sulfosuccinic acid monoalkyl polyoxyethyl esters with 8 to 18 carbon atoms in the alkyl group and 1 to 10 oxyethyl groups.

6. The cleansing composition as claimed in claim 1, wherein the at least one non-ionic surfactant is selected from the group consisting of polyethoxylated carboxylic acid esters with a chain length from 8 to 30 carbon atoms and a degree of ethoxylation from 5 to 50, ethoxylated glyceryl carboxylic acid esters with a degree of ethoxylation from 2 to 20, and alkyl oligoglucosides with 8 to 16 carbon atoms in the alkyl group.

7. The cleansing composition as claimed in claim 1 further comprising a carboxylic acid selected from the group consisting of myristic acid, coconut acid, oleic acid, elaidic acid, petroselinic acid, linoleic acid, linolenic acid, elaeostearic acid, arachidic acid, gadoleic acid, behenic acid, erucic acid, lignoceric acid, cerotic acid, and mixtures thereof.

8. The cleansing composition as claimed in claim 1, wherein the cleansing composition also includes at least one hair- and/or skin-conditioning active ingredient, wherein the active ingredient is selected from the group consisting of oil components, plant extracts and humectants.

9. The cleansing composition as claimed in claim 1, wherein the cleansing composition has a pH value in the range from 4 to 6.

10. A cosmetic, mousse-like cleansing composition comprising:
    a) 0.1 to 30 wt. %, based on the total weight of the cleansing composition, of a surfactant selected from the group consisting of an anionic surfactant, a non-ionic surfactant, zwitterionic surfactant, or mixtures thereof,
    b) a carboxylic acid selected from the group consisting of stearic acid, palmitic acid, and mixtures thereof, in an amount from 9 to 30 wt. % based on the total weight of the cleansing composition,
    c) a non-ionic polymer consisting of a polyethylene glycol with a mean molecular weight of 600,000 to 4,000,000 daltons in a quantity from 0.1 to 1 wt. % based on the total weight of the cleansing composition,
    d) 0.01 to 3 wt. % of one or more naturally derived fatty alcohols selected from the group consisting of decanol, octanol, octenol, dodecenol, decenol, octadienol, dodecadienol, decadienol, oleyl alcohol, erucic alcohol, ricinolyl alcohol, stearyl alcohol, isostearyl alcohol, cetyl alcohol, lauryl alcohol, myristyl alcohol, arachidyl alcohol, caprylic alcohol, capric alcohol, linoleyl alcohol, linolenyl alcohol and behenyl alcohol, Guerbet alcohols thereof and mixtures thereof,
    wherein the cosmetic cleansing composition does not contain a cationic polymer or a propellant, is a foamed mousse, and has a viscosity of 5,000 mPas to 15,000 mPas.

* * * * *